United States Patent
Rammacher

[11] Patent Number: 6,001,086
[45] Date of Patent: Dec. 14, 1999

[54] DEVICE FOR REMOVING URINE AND/OR FECES

[76] Inventor: Hans-Dieter Rammacher, Hirschberger-Str. 27, Burgthann, Germany, D-90559

[21] Appl. No.: 08/930,880
[22] PCT Filed: Feb. 19, 1997
[86] PCT No.: PCT/EP97/00782
§ 371 Date: Sep. 30, 1997
§ 102(e) Date: Sep. 30, 1997
[87] PCT Pub. No.: WO97/31161
PCT Pub. Date: Aug. 28, 1997

[30] Foreign Application Priority Data

Feb. 23, 1996 [DE] Germany .................. 196 06 751

[51] Int. Cl.[6] .................. A61M 1/00; A61F 5/44
[52] U.S. Cl. .................. 604/327; 604/349; 604/351
[58] Field of Search .................. 604/349–353, 604/327

[56] References Cited

U.S. PATENT DOCUMENTS

| 4,319,573 | 3/1982 | Whitlock . | |
|---|---|---|---|
| 4,631,061 | 12/1986 | Martin . | |
| 4,713,067 | 12/1987 | Rothenberg et al. | 604/349 |
| 4,750,219 | 6/1988 | Williams . | |
| 4,840,625 | 6/1989 | Bell | 604/352 |
| 5,616,138 | 4/1997 | Propp | 604/350 |

FOREIGN PATENT DOCUMENTS

| 0 610 638 | 8/1994 | European Pat. Off. . |
| 0 676 508 | 10/1995 | European Pat. Off. . |

Primary Examiner—Mark O. Polutta
Attorney, Agent, or Firm—Collard & Roe, PC.

[57] ABSTRACT

With a device for removing urine and/or feces, for example in connection with sick and infirm people, simple and safe removal is accomplished with a bag (1) with a face-side insertion opening for the genital organ or feces, such opening being tightly connected with a tube line (7, 7'), whereby the tube line (7, 7') is connected with the end facing away from the bag (1) with the suction side of a motor-driven, self-aspirating fluid pump (9), the latter feeding with the pressure side via tube line (7") into the drain pipe (13) of a washbowl (14) or the like.

18 Claims, 3 Drawing Sheets

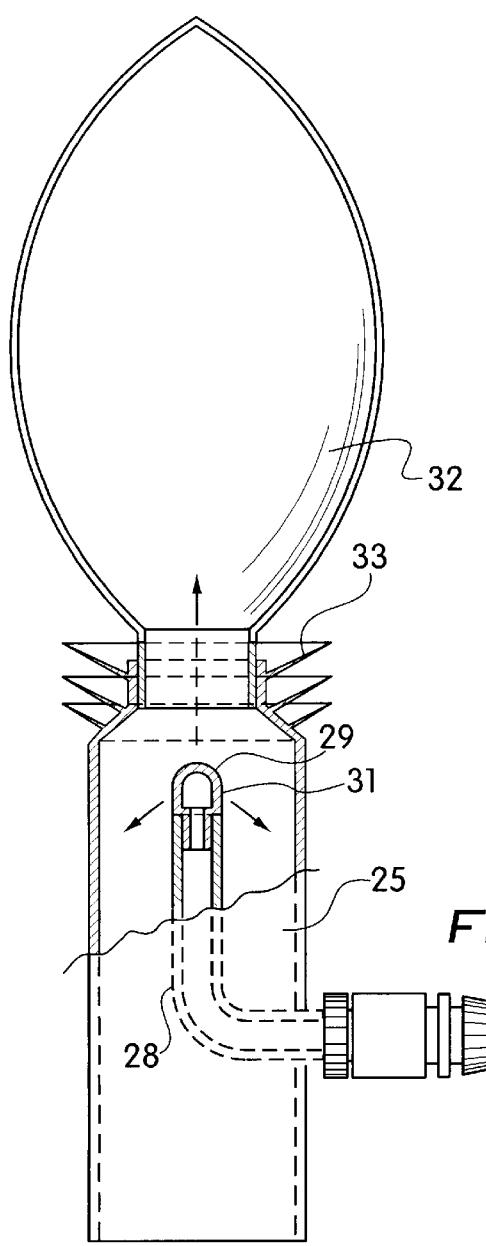
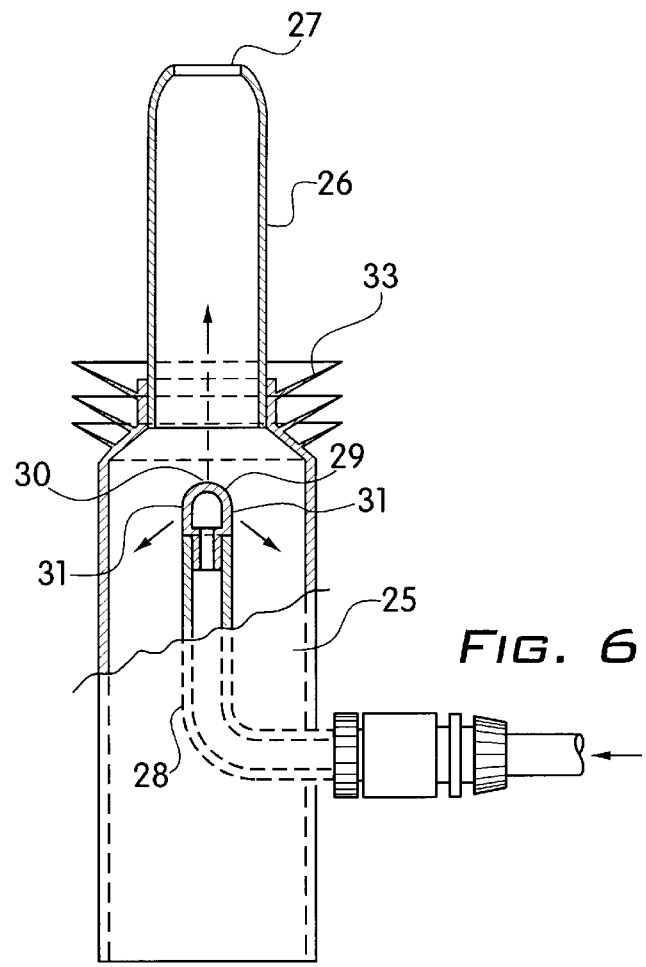
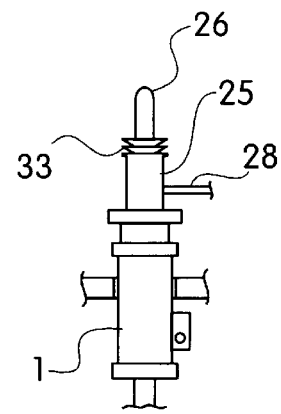
FIG. 6
FIG. 7
FIG. 8

DEVICE FOR REMOVING URINE AND/OR FECES

The invention relates to a device for removing urine and/or feces, for example in connection with sick and infirm persons.

BACKGROUND OF THE INVENTION

Devices for urinal care are known, in which the urine is removed by means of a condom and discharged into a leg pouch via a hose section. Apart from the fact that the leg pouch has to be emptied periodically in a troublesome way, empyying of the leg pouch is often not manageable in a hygienically clean and safe way, so that annoyance caused by bad odor is unavoidable. Further, emptying of the leg pouch often requires additional assistance. Moreover, the known devices do not permit removal of feces due to poor flowability of the latter.

The problem of the invention is to create measures for simple and safe removal of urine and feces.

According to the invention, said problem is solved by a quiver-like bag with an inlet opening on the face side for inserting the genital organ or feces, such bag being tightly connected with a tube line which, with the end facing away from the bag, rests against the suction line of a motor-driven, self-aspirating fluid pump feeding with the pressure side into a drain pipe of a washbowl or the like. Preferably, the pressure side of the fluid pump feeds into the drain pipe of the washbowl via a T-shaped piece of pipe. The flexible pipeline may be usefully formed in this connection by a hose or the like, the latter being detachably fixed on the bag or engaging the latter by means of a disconnectable coupling element. Furthermore, it is conceivable that the hose has a disconnectable separation point disposed with a spacing from the bag and the fluid pump, such separation point being lackable and releasable by a coupling element, whereby the coupling elements are designed in the form of quick-action couplings. In this way, a closed conduit system is formed, and it is assured that urine or feces are continuously discharged, whereby transport operations for transporting collection containers or the like are dispensed with. Urine or feces are removed by suction in a clean way by means of the vacuum adjusted in the hose, whereby no unintended or undesirable discharge of urine or feces via the inlet opening to the outside will occur. Finally, the closed conduit system, furthermore, will not cause any annoyance due to bad odor, and spilling of urine or the like is impossible.

For developing the device further, provision is made that the bag or the adjacent hose section has a manually actuated ON/OFF-switch for the driving motor of the fluid pump. In this way, the device can be put into operation by the person using it at any desired time for discharging urine or feces. In addition, it is possible to equip the bag with a pulse transmitter responding to fluid or moisture, whereby the pulses of such transmitter are used for automatically switching the driving motor of the fluid pump on or off. Moreover, it is conceivable that the driving motor of the fluid pump is periodically automatically switched on or off depending on time, using a time-switch, whereby discharge of urine and feces is made possible also for disabled and helpless persons. Furthermore, it is proposed to make the driving motor of the fluid pump remotely controllable, e.g. by actuating it by infrared pulses for switching the device on and off.

For developing the device further, provision is made that the vacuum in the part of the hose on the suction side is manually or automatically changeable or controllable, so that the vacuum can be adapted to the substances such as urine or feces to be discharged.

Furthermore, provision is made that a flexible flushing conduit connected with the pressure water mains, for example a hose is freely or rigidly and substantially tightly attached to the open side of the bag in order to keep the latter, the hose and the fluid pump clean and odorless. The flushing conduit can be connected with the pressure water mains in any desired way. Preferably, the flushing conduit is particularly connectable with the pressure water pipeline leading to the washbowl or the like via a valve, for example an angle valve. So as to avoid complications caused by pressure of the water mains or failure of the fluid pump, the flushing conduit and/or the hose are equipped with a reflux stop valve. Furthermore, it is conceivable to associate a reservoir for disinfectants or fragrances with the flushing conduit, or to arrange such reservoir in said conduit, such reservoir continuously or periodically dispensing disinfectant into the flushing water, by manual control or continuously or automatically at periodic intervals.

Furthermore, provision is made that the bag has a circular insertion opening and a circuit cross section over its entire length. It is advantageous if the bag has a circular insertion opening adjoined by the remaining part of the bag in a flattened form. In this way, the bag can be secured on the leg of the user without causing pieces of garment or the like to bulge, so that using the bag remains invisible from the outside. Furthermore, it is possible to detachably secure the bag and/or the hose and/or the flushing conduit on parts of the body, for example on the leg of the user by means of at least one belt, band or the like fitted with a closing buckle. It is understood that the bag can be supported on parts of the body of the user also in other ways, for example via shoulder belts.

So as to assure safe transfer of urine or feces into the bag, the latter is fitted within the zone of its insertion opening on the inside with a sleeve-lie sealing gasket, which is rigidly or exchangeably toghtly fixed in the bag and has sealing lips all around the inner circumferential surface, such lips extending circumferentially one on top of the other with axial spacings, whereas annular sealing beads are formed on the outer circumferential surface of the gasket. The sealing lips preferably extend slanted inwardly and downwardly and, together with an O-ring secured in the bag, prevent urine or feces from running out of the bag. The bag itself can be formed by a rigid or a flexible material, for example a plastic material, rubber or the like.

It was found that it is particularly advantageous if the hose and the flushing conduit, in particular, however the latter, jointly feed with the ends facing the bag into a housing-like station, whereby the station is connectable with the bag and has a spraying device or the like connected with the flushing conduit, such device particularly being tightly attachable to or insertable in the insertion opening of the bag.

The insertion opening of the bag usefully has a sealing gasket inserted therein, whereby the clear width of such gasket can be changed for obtaining diameters of different sizes by pushing at least one additional gasket onto it.

Furthermore, removal of feces can be safely facilitated by a tubular adapter tightly fixable on or insertable in the insertion opening, with at least one hollow cylinder insertable with part of its length in the intestine of the user, and with a water tube centrally arranged in the adapter and fitted with a nozzle, such water tube being connectable with the pressure water mains. Centrally, the nozzle has an axial outlet and a number of outlet openings in the circumferential zone for water, the latter outlets being slanted outwardly against the water feed. It was found that the water exiting from the central nozzle softens and crushes the feces, whereas the water exiting from the slanted nozzles effects transport of the feces in the adapter and on into the bad. So as to prevent feces from leaking out, the adapter and/or the cylinder are/is fitted on the outside with annular sealing lips. According to a further development, the adapter, which is advantageously Exchangeably fixed on the bag especially for cleaning purposes, for example by friction grip, can be designed also in such a way that it and the bag form one piece.

With the bag, furthermore, provision is made for a bowl-shaped receiving container for removing feces, such container being attachable or insertable by plugging, and its receiving space being connected with the interior space of the adapter, whereby the latter also a water tube fitted with a nozzle and attachable to the pressure water mains.

Finally, it is conforming to the idea of the invention if, according to another modified embodiment of the device, the fluid pump is omitted, so that urine or feces are transported by action of gravity from the bag via the hose line directly into the drain tube of the washbowl. Precondition for this is that the bag or adapter is disposed or kept higher than the point of inflow on the drain pipe of the washbowl, and that urine or feces can be discharged in accordance with the design of the communicating tube.

The exemplified embodiments with the features important to the invention show how the latter can be realized. In the drawing,

BRIEF DESCRIPTION OF THE DRAWINGS

FIG. 6 shows a lateral, partly sectional view of an adapter;

FIG. 7 shows a lateral, partly sectional and enlarged view of an adapter according to another design; and FIG. 8 shows a reduced lateral view of a bag with an adapter.

DESCRIPTION OF THE PREFERRED EMBODIMENTS

Figure 1:
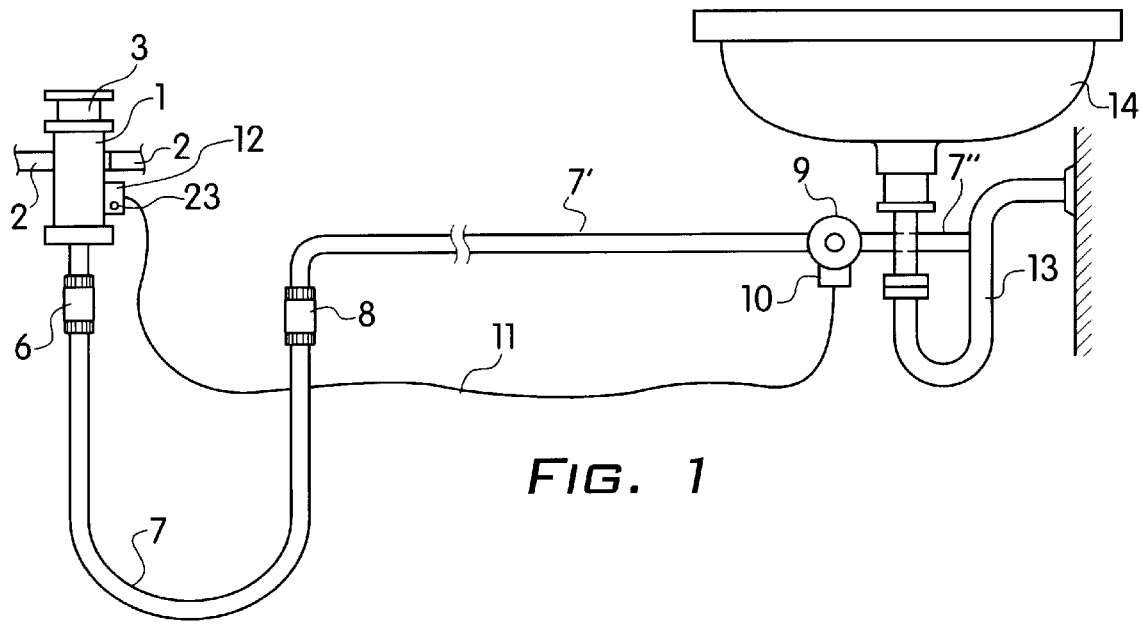
FIG. 1 shows a lateral view of a device.
Figure 2:
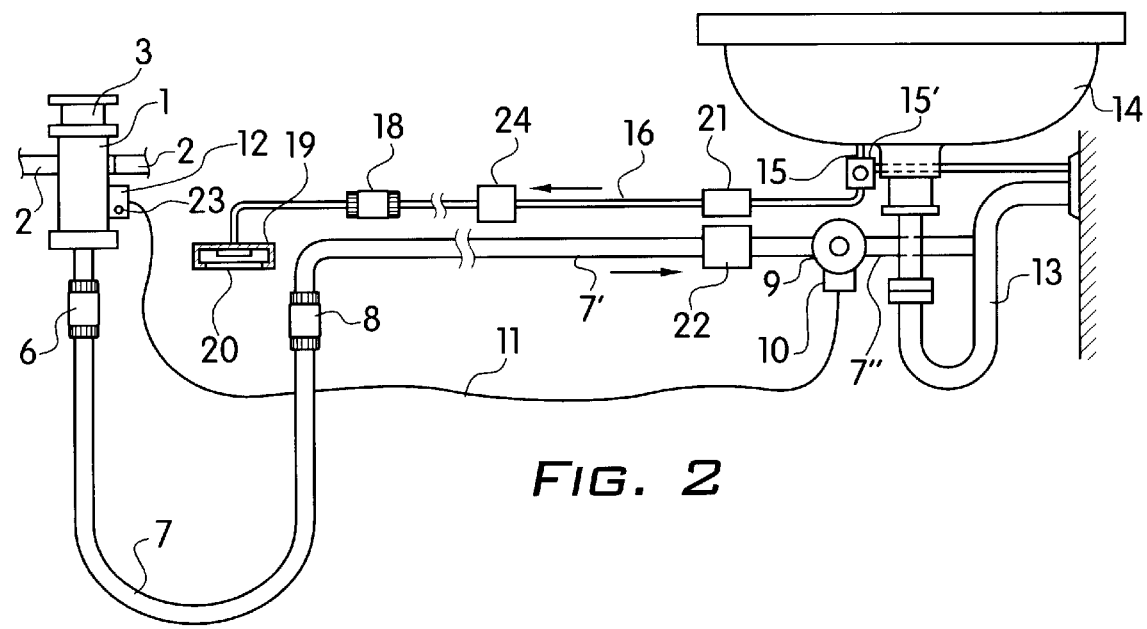
FIG. 2 shows a lateral view of a modified embodiment of a device.
Figure 3:
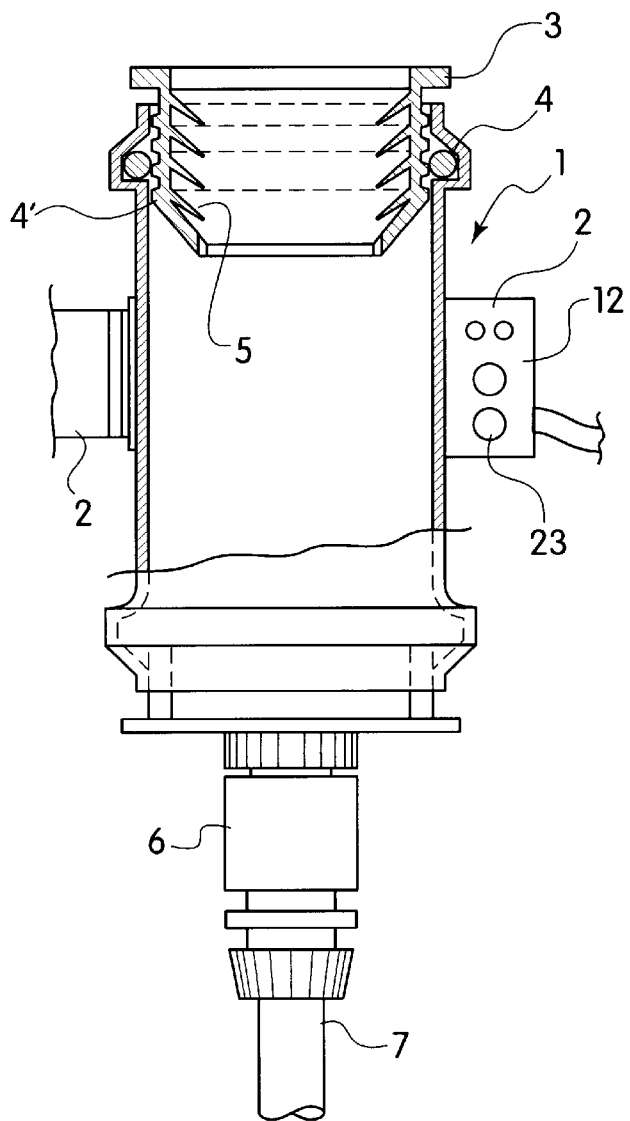
FIG. 3 shows an enlarged lateral, partly section view of a bag.

The device according to FIGS. 1 and 2 has a cylindrical bag 1 for receiving, for example the genital organ of a user, such bag being fixable on the leg (not shown) of the user by the holding straps 2. At its insertion end, bag 1 is fitted with a sealing gasket 3 which, according to FIG. 3, is pressed into bag 1 and sealed against bag 1 by an O-ring 4 and sealing beads 4'. On the inner circumferential surface, sealing gasket 3 has a number of annular sealing lips 5 one on top of the other, which are slanted inwardly and directed downwardly with their thickness decreasing toward the free end. Sealing gasket 3 is made of a flexible or springy elastic material, for example rubber. In the exemplified embodiments, bag is is followed by means of a quick-action coupling 6 by a hose section 7, and by way of a quick-action coupling 8 by another hose section 7' which, with the end remote from bag 1, is connected with the suction side of a fluid pump 9. Fluid pump is is designed as a self-aspirating pump. Driving motor 10 of said pump is connected via a cable 11 with an electrical switching device 12 arranged on bag 1. The pressure side of fluid pump 9 is connected with drain pipe 13 of a washbowl 14 via a hose section 7". It is understood that hose section 7" is connectable also with the drain pipes of other suitable devices.

When used, urine can be removed by suction from bag 1 via the hose sections 7 and 7' and fluid pump 9 and discharged via hose section 7" into the drain pipe in order to flow from there into the sewer system. The vacuum generated by fluid pump 9 in bag 1 and hose sections 7, 7' prevents urine from unintentionally exiting from bag 1 into the space.

With the device according to FIG. 2, where bag 1, hose sections 7, 7' and fluid pump 9 have the same design per se, the device is connected with pressure water mains 15 of washbowl 14, and a flushing conduit 16 is connected with the water mains via an angle valve 15'. Flushing conduit 16 is connected with a housing-like station 19 via a quick-action coupling 18, said station having a shower device 20. Station 19 can be plugged onto bag 1 from the top, and by releasing flushing conduit 16, bag 1 and hose sections 7, 7', fluid pump 19 as well as hose section 7" can be cleaned. A reflux stoop valve 21 is arranged in flushing conduit 16. Provision can be made for another reflux stop valve 22 also in hose section 7' in order to prevent return flow of urine or feces in the direction of bag 1. It is understood that instead of manual switch 23 of switching device 12, driving motor 10 of the fluid pump can be automatically activated periodically as well. For such purpose, it is possible to use, for example a time relay (not shown). Furthermore, provision is made for starting driving motor 10 by electric pulses with remote control, e.g. infrared.

It is possible to arrange in flushing conduit 16 a reservoir 24 for disinfectants.

Figure 4:
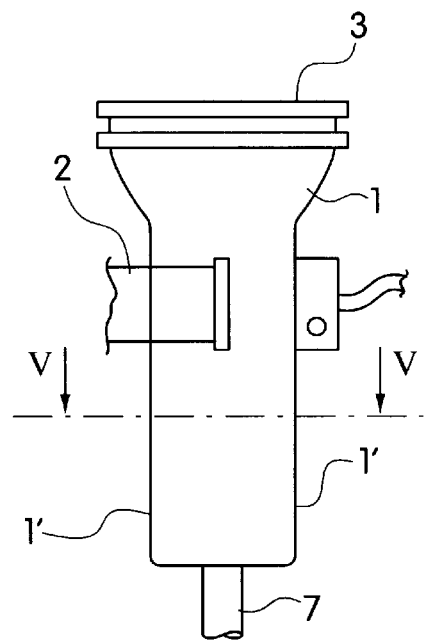
FIG. 4 shows a bag according to another design, by a reduced view.
Figure 5:
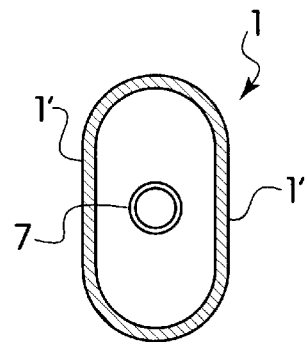
FIG. 5 shows a section according to line V—V in FIG. 4.

With bag 1 according to FIGS. 4 and 5, a circular insertion opening is followed by wall sections having the flattenings 1', which facilitate the application of the device and make it optically invisible.

In FIGS. 6 and 8, bag 1 is fitted with a plugged-on adapter 25 supporting a hollow cylinder 26, which is insertable in the intestine (now shown) of the user and which has an inlet aperture 27 for feces. Adapter 25 receives a water tube 28 with a nozzle 29, whereby nozzle 29 is provided with a central axial water outlet aperture 30 and a plurality, for example three downwardly and outwardly slanted water exit apertures 31. The water exiting from aperture 30 serves for dissolving and crushing feces, and the water exiting from apertures 31 for transporting feces in the direction of bag 1 and on.

In FIG. 7, a bowl-shaped receiving container 32 for feces is plugged onto bag 1, said container being connected with the inside space 25' of adapter 25. In this embodiment, too, adapter 25 is equipped with a water tube 28 with nozzle 29.

I claim:

1. A device for removing urine or feces, comprising:
   (a) a bag having an opening on the face side for inserting a genital organ of a sick or infirm person;
   (b) a flexible tube conduit tightly connected with the bag via which the urine can be delivered by vacuum to a receiving device by means of a pump driven by an electric motor;
   the bag being connected with the tube conduit to the suction side of the pump,
   said pump feeding with the pressure side via a flexible tube conduit into the drain pipe of the receiving device;

(c) a flexible flushing conduit connected with a pressurized water main, said flushing conduit being tightly connected to the bag; and (d) retaining straps to fix the bag to the body of the person.

2. A device according to claim 1, wherein the flexible tube and flushing conduits are formed by hoses or hose sections.

3. A device according to claim 1, wherein the bag or an adjacent hose section of the tube conduit has a manually actuated ON/OFF switch for the driving motor of the pump.

4. A device according to claim 1, wherein the bag has a pulse transmitter responding to fluid or moisture, the pulses of such transmitter being usable for automatically switching the driving motor of the pump on and off.

5. A device according to claim 1, wherein the driving motor of the pump is periodically automatically switchable on and off dependent upon time by means of a time switch.

6. A device according to claim 1, wherein the vacuum in the suction-side of the tube conduit is manually or automatically variable or controllable.

7. A device according to claim 1, wherein the flushing conduit is connectable by way of a valve with the pressure water main leading to the receiving device.

8. A device according to claim 1, wherein the flushing conduit or the tube conduit has a reflux stop valve.

9. A device according to claim 1, wherein a reservoir for disinfectants or odor fresheners is associated with or arranged in the flushing conduit, such reservoir continuously or periodically by manual control or automatically dispensing disinfectants or fragrances into the flushing water.

10. A device according to claim 1, wherein the bag, within the zone of the insertion opening, has on the inside, a sleeve-like sealing gasket rigidly or exchangeably secured tightly on the bag; the sealing gasket having, on the inner circumferential surface sealing lips circumferentially extending with axial spacing one on top of the other; and sealing beads or the like are formed on the outer circumferential surface of the sealing gasket.

11. A device according to claim 1, wherein the flushing conduit feeds into a housing-like station; the stations being connectable with the bag and having a spraying device or the like connected with the flushing conduit; and wherein such device is particularly tightly mountable on or insertable in the insertion opening of the bag.

12. A device according to claim 10, wherein the clear width of the sealing gasket arranged in the insertion opening of the bag can be reduced in diameter by inserting at least one additional sealing gasket.

13. A device according to claim 1, further comprising an adapter tightly mountable on or insertable in the insertion opening of the bag, with a hollow cylinder being insertable in the intestine of the user with part of its length, and with a water tube having a nozzle and being connectable with the pressure water main, said tube being centrally arranged in the adapter.

14. A device according to claim 13, wherein the nozzle centrally has an axial outlet aperture and within the circumferential zone a number of outwardly-slated apertures directed against the water feed for water.

15. A device according to claim 13, wherein the adapter or the hollow cylinder has on the outside annularly shaped sealing lips.

16. A device according to claim 13, wherein the adapter and the bag are designed as forming one (1) piece.

17. A device according to claim 1, further comprising a bowl-like receiving container tightly plugable onto or into the insertion opening of the bag; the receiving space of the receiving container being communicatively connected with the interior space of the adapter; the adapter centrally receiving a water tube having a nozzle and being connectable with the pressure water main.

18. A device according to claim 17, wherein the nozzle centrally has an axial outlet aperture and within the circumferential zone a number of slanted outlet apertures for water, said slanted outlet apertures being directed outwardly or against the water in-feed.

* * * * *